United States Patent [19]

Bielefeldt et al.

[11] Patent Number: 5,072,030

[45] Date of Patent: Dec. 10, 1991

[54] PROCESS FOR THE FLUORINATION OF ACRYLIC ACID AND DERIVATIVES THEREOF AND NOVEL FLUORINATED ESTERS OF 2,3-DIFLUOROPROPIONIC ACID

[75] Inventors: Dietmar Bielefeldt, Ratingen; Karl-Rudolf Gassen, Odenthal; Walter Lange, Cologne, all of Fed. Rep. of Germany

[73] Assignee: Bayer Aktiengesellschaft, Leverkusen, Fed. Rep. of Germany

[21] Appl. No.: 478,330

[22] Filed: Feb. 12, 1990

[30] Foreign Application Priority Data

Feb. 16, 1989 [DE] Fed. Rep. of Germany ....... 3904707

[51] Int. Cl.$^5$ .............................................. C07C 69/63
[52] U.S. Cl. .................................... 560/227; 562/605; 562/864
[58] Field of Search ................. 560/227; 562/605, 864

[56] References Cited

U.S. PATENT DOCUMENTS 2,680,764  6/1954  Ney, Jr. ............................... 560/227

FOREIGN PATENT DOCUMENTS 721180  5/1942  Fed. Rep. of Germany .
730328  5/1955  United Kingdom .
794360  4/1958  United Kingdom .

*Primary Examiner*—Paul J. Killos
*Attorney, Agent, or Firm*—Sprung Horn Kramer & Woods

[57] ABSTRACT

Difluoropropionic acid and derivatives thereof are prepared by bringing elemental fluorine in the presence of a solvent into an addition reaction with appropriate acrylic acids or derivatives thereof. In this way, it is also possible to obtain novel fluorinated esters of 2,3-difluoropropionic acid.

7 Claims, No Drawings

PROCESS FOR THE FLUORINATION OF ACRYLIC ACID AND DERIVATIVES THEREOF AND NOVEL FLUORINATED ESTERS OF 2,3-DIFLUOROPROPIONIC ACID

The present invention relates to a process for the preparation of difluoropropionic acid and derivatives thereof by fluorination of the corresponding acrylic acids or acrylic acid derivatives and novel fluorinated esters of 2,3-difluoropropionic acid accessible in this manner.

Polymeric α-fluoroacrylic acid derivatives have good optical and mechanical properties. They are therefore suitable for the production of optical devices (for example lenses, compact discs) and of fibres and membranes (cf. for example EP-A1 0 249 867, EP-A2 0 203 462 and U.S. Pat. No. 4,297,466). Until now these materials have not however been used commercially because processes which are economical and can be operated industrially for the preparation of α-fluoroacrylic acid and derivatives thereof have hitherto not been available. The known processes require a large number of reaction steps and/or produce the desired products only in low yields (cf. for example Zh. Org. Khim. 28, 1173 (1987)).

A process for the fluorination of acrylic acid and derivatives thereof has now been found which is characterized in that elemental fluorine is brought in the presence of a solvent into an addition reaction with the C=C double bond of acrylic acid or of a derivative thereof having the formula (II)

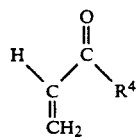
(II)

in which
R$^4$ represents OH, a halogen atom or a substituted or unsubstituted radical from the group C$_1$- to C$_{20}$-alkoxy, C$_3$- to C$_{20}$-cycloalkoxy, C$_6$- to C$_{20}$-aryloxy and C$_7$- to C$_{20}$-aralkoxy and in this way 2,3-difluoropropionic acid or a derivative thereof having the formula (III) is obtained

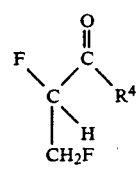
(III)

in which
R$^4$ has the meaning given in formula (II).

By eliminating hydrogen fluoride, for example by adding a base, and, if desired by forming another derivative before, during and/or after the elimination of hydrogen fluoride, it is possible to convert compounds of the formula (III) into compounds of the formula (I)

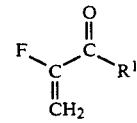
(I)

in which
R$^1$ represents NR$^2$R$^3$ or OR$^2$, R$^2$ being hydrogen or a substituted or unsubstituted radical from the group C$_1$- to C$_{20}$-alkyl, C$_3$- to C$_{20}$-cycloalkyl, C$_6$- to C$_{20}$-aryl and C$_7$- to C$_{20}$-aralkyl and R$^3$ has the same scope of meaning as R$^2$ and may be identical with or different from R$^2$.

If in formula (I) R$^2$ and/or R$^3$ represent a substituted or unsubstituted radical, suitable substituents are preferably C$_1$- to C$_4$-alkyl radicals and halogen atoms, particularly fluorine and chlorine atoms.

If in the compounds of formula (II) which are to be used according to the invention R$^4$ represents halogen, the compounds are acryloyl halides. Those preferred are acryloyl fluoride and acryloyl chloride. These are readily accessible. The use of acryloyl chloride (formula (II), R$^4$=Cl) is particularly preferred.

If in formula (II) R$^4$ represents a substituted or unsubstituted alkoxy, cycloalkoxy, aryloxy or aralkoxy radical, halogen substituents, particularly fluorine and chlorine are preferred. Fluorine is particularly preferred. Furthermore, preference is given to partially fluorinated aliphatic C$_4$- to C$_{20}$-alkoxy radicals, particularly C$_4$- to C$_7$-alkoxy radicals, which are straight chain, branched chain or cyclic.

Compounds of the formula (II) with R$^4$=alkoxy, cycloalkoxy, aryloxy or aralkoxy radicals which may if desired be substituted by halogen are readily accessible (cf. for example B. Boutevin, G. Rigal, A. Rousseau; J. Fluorine Chem. 38, 47 (1988)).

The reaction with elemental fluorine is an essential feature of the present invention. This reaction may for example be carried out at temperatures in the range of −100° to +30° C. Preference is given to temperatures in the range of −78° to ±0° C. It is preferable to use 0.8 to 1.5 moles of elemental fluorine per mole of compound of the formula (II). Suitable solvents for this reaction are in particular fluorinated, if desired also chlorinated, hydrocarbons with melting points below +20° C. CFCl$_3$ is a preferred solvent.

Elemental fluorine is generally used mixed with an inert gas. Examples of inert gases of this type are nitrogen and helium. The fluorine/inert gas mixtures may for example contain 0.5 to 50% by weight of fluorine, and preferably contain from 1 to 10% by weight of fluorine. The reaction with fluorine may for example be carried out in vessels which are produced from polyethylene or polyolefins containing fluorine, for example polytetrafluoroethylene, or lined with these materials. It is also possible to use glass, stainless steel, nickel, nickel alloys, copper and copper alloys. In a particular embodiment of the process according to the invention the fluorination is carried out in the presence of an HF scavenger. The following are suitable for this for example: alkali metal and alkaline earth metal fluorides, alkali metal and alkaline earth metal oxides and aluminium oxides. Preference is given to sodium fluoride and aluminium oxide.

The use of the reaction according to the invention with elemental fluorine produces 2,3-difluoropropionic acid or a derivative thereof (cf. formula (III)) in good yields. Undesired alterations to the radical R$^4$ and other side reactions occur only to a limited extent. The compound of the formula (III) obtained can be isolated for example by filtering off solid components which may be present in the reaction mixture and then distilling off the solvent. The compound of formula (III) may be further purified by distillation if desired.

The products of the formula (III) which are obtainable in this way can be converted into α-fluoroacrylic acid derivatives or into α-fluoroacrylic acid. The conversion of the 2,3-difluoropropionic acid group into an α-fluoroacrylic acid group can be achieved with the elimination of HF by adding a base.

Suitable bases for this purpose are for example organic amines, alcoholates, alkali metal and/or alkaline earth metal hydroxides. Preference is given to tertiary amines, such as N,N-dimethylaniline, triethylamine, 1,5-diazabicyclo[4.3.0]non-5-ene (DBN) and 1,8-diazabicyclo[5.4.0]undec-7-ene (DBU).

The elimination of HF requires stoichiometrically one equivalent of base per mole of compound of formula (III) or of a derivative thereof. 0.8 to 1.2 equivalents of base are therefore generally used for the elimination of HF. In certain cases, the use of greater amounts of base is indicated. If for example an acid halide, for example $CH_2F—CHF—CO—Cl$ is used in the HF elimination with simultaneous formation of a derivative, a further equivalent of base is necessary. If the purpose is to prepare acid amides (cf. formula (I), $R^1=NR^2R^3$) one equivalent of the corresponding amine $HNR^2R^3$ is stoichiometrically necessary in order to introduce the $NR^2R^3$ group. It is also possible to use this amine to carry out the HF elimination. A further equivalent of the amine is then necessary. If the corresponding amine $HNR^2R^3$ used for introducing an $NR^2R^3$ group is in salt form, for example as the hydrochloride a further equivalent of base is needed to release the amine from the salt. In all these cases, the use of correspondingly greater amounts of the base than 0.8 to 1.2 equivalents is indicated, since the side reactions mentioned often run parallel to HF elimination.

The elimination of HF may for example be carried out at temperatures in the range of $-78°$ to $+100°$ C. Preference is given to temperatures in the range from $-20°$ to $+55°$ C.

Suitable solvents are those which are conventionally used in the esterification or the preparation of amides from carbonyl compounds. Preference is given to ethers, halogenated hydrocarbons and aromatic solvents.

With the measures hitherto described, compounds of the formula (II) can be converted into compounds of the formula (I) if $R^4$ in formula (II) is identical with $R^1$ in formula (I). Thus it is possible for example to use an acrylate ester (formula (II), $R^4$ not being halogen and not being OH) to prepare the analogous α-fluoroacrylate ester (formula (I), $R^1=OR^2$, $R^2$ not being hydrogen).

In order to prepare other compounds of the formula (I) derivatization can be carried out before, during and/or after the HF elimination. These can be carried out by methods known per se. Examples of the type of reactions which can be carried out before, during and/or after the elimination of HF are listed below:

1) 2,3-Difluoropropionyl halides (formula (III), $R^4=$halogen) can be converted by reacting with an alcohol of the formula $HOR^2$ ($R^2$ not being hydrogen, otherwise as given in the case of formula (I)) into the corresponding 2,3-difluoropropionic ester from which compounds of the formula (I) with $R^1=OR^2$ ($R^2$ not being hydrogen) are accessible by HF elimination. This mode of operation is advantageous for example if it is intended to prepare compounds of the formula (I) which contain a radical $OR^2$ which is accessible with difficulty and therefore expensive, and which has a tendency to undergo side reactions during fluorination.

2) α-Fluoroacryloyl halides of the type $CH_2=CF—CO—Hal$ can be converted by reacting with an alcohol of the formula $HOR^2$ ($R^2$ not being hydrogen, otherwise being as given for formula (I)) into the corresponding α-fluoroacrylate ester (formula (I), $R^1=OR^2$, $R^2$ not being hydrogen). This mode of operation is for example advantageous if it is intended to prepare compounds of the formula (I) which contain a radical $OR^2$ which is accessible with difficulty and therefore expensive, and which has a tendency to undergo side reactions during HF elimination.

3) 2,3-Difluoropropionic esters (formula (III), $R^4$ not being halogen, otherwise as given in formula (II)) can be transesterified with an alcohol of the formula $HOR^2$ ($R^2$ not being hydrogen, otherwise being as given in formula (I)) and converted by subsequent HF elimination into compounds of the formula (I) with $R^1=OR^2$ ($R^2$ not being hydrogen). Before being reacted with the alcohol of the formula $HOR^2$ the 2,3-difluoropropionic ester used may, if desired, be hydrolysed to the free acid (for example with nitric acid) and/or converted into the acid chloride. This mode of operation is advantageous for example if it is intended to prepare compounds of the formula (I) which contain a radical $OR^2$ which tends to undergo side reactions during fluorination.

4) 2,3-Difluoropropionyl halides (formula (III), $R^4=$halogen) can be converted by reaction with an amine of the formula $HNR^2R^3$ ($R^2$ and $R^3$ as given in formula (I)) into the corresponding 2,3-difluoropropionamide from which the corresponding α-fluoroacrylamide (formula (I), $R^1=NR^2R^3$) can be obtained by HF elimination.

5) α-Fluoroacrylamides (formula (I), $R^1=NR^2R^3$) can be obtained from α-fluoroacryloyl halides of the type $CH_2=CF—CO—Hal$ by reaction with an amine of the formula $HNR^2R^3$.

In the manner described, compounds of the formula (I) can be obtained in few reaction steps from readily accessible starting compounds and in good yields. Preference is given to preparing compounds of the formula (I) in which $R^1$ represents a substituted or unsubstituted $C_2$- to $C_{10}$-alkoxyl radical, represents a substituted or unsubstituted $C_3$- to $C_8$-cycloalkoxy radical, represents a substituted or unsubstituted aryloxy radical or represents an amido radical which may if desired be substituted with straight chain or cyclic $C_1$- to $C_{10}$-alkyl groups or halogenoalkyl groups. If substituted radicals are present here, they are preferably those which are substituted by halogen atoms, in particular fluorine atoms and/or chlorine atoms.

The present invention also relates to novel fluorinated esters of 2,3-difluoropropionic acid of the formula (IIIa)

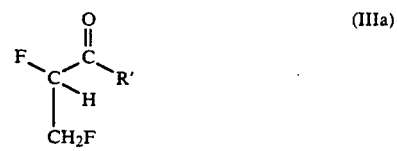

(IIIa)

in which
R' represents a fluorine-substituted $C_1$- to $C_{20}$-alkoxy radical or $C_3$- to $C_{20}$-cycloalkoxy radical.

The alkoxy radicals and cycloalkoxy radicals may if desired contain further substituents other than fluorine, for example chlorine.

EXAMPLES

Example 1

5.6 moles of fluorine (5% strength mixture with nitrogen, inward flow rate 0.5 mole/hr) were introduced to a solution of 560 g (5.6 moles) of ethyl acrylate in 7,000 ml of trichlorofluoromethane at −78° C. The solvent was subsequently distilled off and a product mixture was obtained which contained 31% by weight of unconverted starting material, 6% by weight of ethyl α-fluoroacrylate, 41% by weight of ethyl 2,3-difluoropropionate and 12% by weight of monofluoroethyl 2,3-difluoropropionate.

Example 2

7.5 moles of fluorine (30% strength mixture with helium, inward flow rate 0.5 mole/hr) were introduced into a suspension of 1,114 g (12.3 moles) of acryloyl chloride, 615 g (24.6 moles) of sodium fluoride and 6,000 ml of trichlorofluoromethane at −78° to −65° C. The mixture was then filtered and 2,3-difluoropropionyl chloride was obtained by distillation from the filtrate, having a boiling point of 112° to 113° C. at 1,013 mbar and a purity of 98%.

Example 3

0.15 mole of fluorine was introduced under the same conditions as given in Example 2 to a suspension of 10 g (0.14 mole) of acrylic acid, 10 g (0.24 mole) of sodium fluoride and 100 ml of trichlorofluoromethane. The mixture was then filtered and the solvent was distilled off from the filtrate. In this manner, 8.5 g of 2,3-difluoropropionic acid were obtained at a purity of 90%.

Example 4

2,340 g of a crude fluorinated mixture obtained as in Example 1 were stirred with 5,000 ml of 50% by weight strength nitric acid at room temperature until gas evolution ended, which took 16 hours. The reaction mixture was then worked up by distillation at 16 mbar. 2,3-Difluoropropionic acid with a boiling point of 82° to 85° C. at 16 mbar and a melting point of 36° to 38° C. was obtained in a yield of 394 g. The $^{19}$F-nuclear magnetic resonance spectrum showed characteristic lines at 119 ppm and 152 ppm.

Example 5

220 g (2.0 moles) of the 2,3-difluoropropionic acid obtained according to Example 4 were stirred with 350 g (2.94 moles) of thionyl chloride at 90° C. When the evolution of gas became weaker, 0.5 ml of dimethylformamide was added and the mixture was stirred further until gas evolution ended (a total of 18 hours). The reaction mixture was then distilled. 229 g of 2,3-difluoropropionyl chloride were obtained having a boiling point of 112° to 113° C. and a purity of 98%.

Example 6

34.6 g (0.27 mole) of 2,3-difluoropropanoyl chloride were added dropwise to a solution of 50 g (0.27 mole) of 2,2,3,4,4,4-hexafluoro-1-butanol and 21.6 g (0.27 mole) of pyridine in 200 ml of dry tetrachloromethane. Stirring was continued for a further 1 hour and then the mixture was poured into water, extracted, dried and distilled. In this manner, 56 g of 2,2,3,4,4,4-hexafluorobutyl 2,3-difluoropropionate were obtained having a melting point of 84° to 86° C. at 20 mbar. The purity of the product prepared was 95% (determined by gas chromatography).

Example 7

To a solution of 55.5 g (0.2 mole) of 2,3-difluoropropionic acid-2,2,3,4,4,4-hexafluorobutylester and a spatula tipful of hydroquinone in 550 ml of dry diethyl ether there was added dropwise at −10° C. a solution of 23 g (0.19 mole) of 1,5-diazabicyclo[4.3.0]non-5-ene in 140 ml of dry diethyl ether. The solvent was then distilled off in vacuo in the cold and the residue remaining was fractionated. In this way, 23 g of 2,2,3,4,4,4-hexafluorobutyl α-fluoroacrylate were obtained having a boiling point of 53° to 54° C. at 20 mbar and a purity of 98%.

What is claimed is:

1. A process for the fluorination of acrylic acid and derivatives thereof, in which elemental fluorine, in the form of a fluorine/inert gas mixture which contains 0.5 to 50% by weight of elemental fluorine, is brought in the presence of a solvent into an addition reaction with the C=C double bond of acrylic acid or of a derivative thereof of the formula (II)

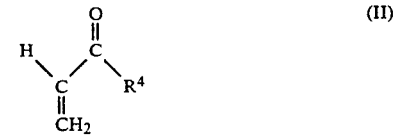

in which
R$^4$ represents OH, a halogen atom or a substituted or unsubstituted radical from the group $C_1$- to $C_{20}$-alkoxy, $C_3$- to $C_{20}$-cycloalkoxy, $C_6$- to $C_{20}$-aryloxy and $C_7$- to $C_{20}$-aralkoxy, at a temperature of −100° to +30° C. and in this way 2,3-difluoropropionic acid or a derivative thereof having the formula (III) is obtained

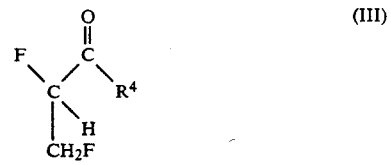

in which
R$^4$ has the meaning given in formula (II).

2. The process of claim 1, in which the compound used of the formula (II) is acryloyl fluoride or acryloyl chloride.

3. The process of claim 1, in which a compound of the formula (II) is used in which R$^4$ represents a partially fluorinated aliphatic straight chain $C_4$- to $C_{20}$-alkoxy radical.

4. The process of claim 1, in which a compound of the formula (II) is used in which R$^4$ represents a partially fluorinated aliphatic branched $C_4$- to $C_{20}$-alkoxy radical.

5. The process of claim 1, in which a compound of the formula (II) is used in which $R^4$ represents a partially fluorinated cyclic aliphatic $C_4$- to $C_{20}$-alkoxy radical.

6. The process of claim 1, in which 0.8 to 1.5 moles of elemental fluorine are used per mole of compound of the formula (II).

7. Fluorinated esters of 2,3-difluoropropionic acid of the formula (IIIa)

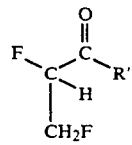

in which
$R^1$ represents a fluorine-substituted $C_1$- to $C_{20}$-alkoxy radical or $C_3$- to $C_{20}$-cycloalkoxy radical.

* * * * *